United States Patent
Bonnette et al.

(10) Patent No.: US 7,615,031 B2
(45) Date of Patent: Nov. 10, 2009

(54) GAS INFLATION/EVACUATION SYSTEM INCORPORATING A MULTIPLE ELEMENT VALVED GUIDEWIRE ASSEMBLY HAVING AN OCCLUSIVE DEVICE

(75) Inventors: Michael J. Bonnette, Minneapolis, MN (US); Richard R. Prather, St. Michael, MN (US); Eric J. Thor, Arden Hills, MN (US)

(73) Assignee: MEDRAD, Inc., Indianola, PA (US)

( * ) Notice: Subject to any disclaimer, the term of this patent is extended or adjusted under 35 U.S.C. 154(b) by 0 days.

(21) Appl. No.: 11/217,546

(22) Filed: Sep. 1, 2005

(65) Prior Publication Data
US 2007/0060881 A1    Mar. 15, 2007

(51) Int. Cl.
*A61M 29/00* (2006.01)
(52) U.S. Cl. ................................. 604/99.01
(58) Field of Classification Search .............. 604/533, 604/96.01, 97.01, 97.02, 97.03, 98.01, 99.01, 604/99.02, 99.03, 99.04, 110.01, 100.03, 604/102.03, 103.04, 103.06, 103.01, 107, 604/912, 914, 915, 528; 606/192, 194, 198
See application file for complete search history.

(56) References Cited

U.S. PATENT DOCUMENTS

| | | | |
|---|---|---|---|
| 3,773,290 A | 11/1973 | Mowery | |
| 3,913,938 A | 10/1975 | Aikawa et al. | |
| 4,122,556 A | 10/1978 | Poler | |
| 4,166,807 A | 9/1979 | Komatsu et al. | |
| 4,332,254 A | 6/1982 | Lundquist | |
| 4,381,765 A | 5/1983 | Burton | |
| 4,467,003 A | 8/1984 | Pallaroni et al. | |
| 4,573,470 A | 3/1986 | Samson et al. | |
| 4,573,966 A | 3/1986 | Weikl et al. | |
| 4,636,195 A | 1/1987 | Wolinsky | |
| 4,646,719 A | 3/1987 | Neuman et al. | |
| 4,651,738 A | 3/1987 | Demer et al. | |
| 4,653,539 A | 3/1987 | Bell | |
| 4,733,652 A | 3/1988 | Kantrowitz et al. | |

(Continued)

FOREIGN PATENT DOCUMENTS

DE    4221126    8/1994

(Continued)

OTHER PUBLICATIONS

Medical Device & Diagnostic Industry, Aug. 1997, Article by Nancy J. Hermanson et al.

(Continued)

*Primary Examiner*—Nicholas D Lucchesi
*Assistant Examiner*—Christopher D Koharski
(74) *Attorney, Agent, or Firm*—James Stevenson; David Schramm

(57) ABSTRACT

A gas inflation/evacuation system incorporating a multiple element valved guidewire assembly having an occlusive device for use in thrombectomy or other vascular procedures includes a multiple element valved guidewire assembly having an occlusive balloon removably and sealingly connectible to an included manifold assembly where a guidewire tube defines a lumen for inflation or deflation of the occlusive balloon. A first syringe for evacuating the lumen and a second syringe for introducing a biocompatible gas into the lumen to inflate the occlusive balloon that is in fluid communication with the lumen a plurality of times are included. A sealing valve arrangement selectively seals the proximal portion of the guidewire tube to control inflated or deflated states of the occlusive balloon.

24 Claims, 10 Drawing Sheets

U.S. PATENT DOCUMENTS

| | | | |
|---|---|---|---|
| 4,748,986 | A | 6/1988 | Morrison et al. |
| 4,757,827 | A | 7/1988 | Buchbinder et al. |
| 4,758,223 | A | 7/1988 | Rydell |
| 4,832,023 | A | 5/1989 | Murphy-Chutorian et al. |
| 4,838,268 | A | 6/1989 | Keith et al. |
| 4,865,587 | A | 9/1989 | Walling |
| 5,014,494 | A | 5/1991 | George |
| 5,059,176 | A | 10/1991 | Winters |
| 5,059,178 | A | 10/1991 | Ya |
| 5,102,395 | A * | 4/1992 | Cheer et al. ............ 604/167.03 |
| 5,106,363 | A | 4/1992 | Nobuyoshi |
| 5,135,482 | A | 8/1992 | Neracher |
| 5,167,239 | A | 12/1992 | Cohen et al. |
| 5,171,221 | A | 12/1992 | Samson |
| 5,176,692 | A | 1/1993 | Wilk et al. |
| 5,195,955 | A | 3/1993 | Don Michael |
| 5,196,245 | A | 3/1993 | DeRudder et al. |
| 5,207,656 | A | 5/1993 | Kranys |
| 5,209,727 | A | 5/1993 | Radisch, Jr. et al. |
| 5,320,604 | A | 6/1994 | Walker et al. |
| 5,324,260 | A | 6/1994 | O'Neill et al. |
| 5,334,153 | A | 8/1994 | McIntyre et al. |
| 5,338,010 | A | 8/1994 | Haupt |
| 5,365,943 | A | 11/1994 | Jansen |
| 5,380,284 | A | 1/1995 | Don Michael |
| 5,399,658 | A | 3/1995 | Archey et al. |
| 5,413,581 | A | 5/1995 | Goy |
| 5,474,194 | A | 12/1995 | Heilman et al. |
| 5,505,699 | A | 4/1996 | Forman et al. |
| 5,514,109 | A | 5/1996 | Mollenauer et al. |
| 5,520,645 | A | 5/1996 | Imran et al. |
| 5,583,047 | A | 12/1996 | Blinka et al. |
| 5,584,843 | A | 12/1996 | Wulfman et al. |
| 5,601,306 | A | 2/1997 | Heyring |
| 5,605,543 | A | 2/1997 | Swanson |
| 5,688,234 | A | 11/1997 | Frisbie |
| 5,713,917 | A | 2/1998 | Leonhardt et al. |
| 5,775,327 | A | 7/1998 | Randolph et al. |
| 5,776,100 | A | 7/1998 | Forman |
| 5,779,688 | A | 7/1998 | Imran et al. |
| 5,792,179 | A | 8/1998 | Sideris |
| 5,794,325 | A | 8/1998 | Falandy |
| 5,795,325 | A | 8/1998 | Valley et al. |
| 5,807,330 | A | 9/1998 | Teitelbaum |
| 5,827,324 | A | 10/1998 | Cassell et al. |
| 5,833,644 | A | 11/1998 | Zadno-Azizi et al. |
| 5,833,650 | A | 11/1998 | Imran |
| 5,843,022 | A | 12/1998 | Willard et al. |
| 5,865,721 | A | 2/1999 | Andrews et al. |
| 5,881,534 | A | 3/1999 | Ahlqvist et al. |
| 5,908,405 | A | 6/1999 | Imran et al. |
| 5,925,016 | A | 7/1999 | Chornenky et al. |
| 5,938,672 | A | 8/1999 | Nash |
| 5,997,558 | A | 12/1999 | Nash |
| 6,009,708 | A | 1/2000 | Miki et al. |
| 6,021,340 | A | 2/2000 | Randolph et al. |
| 6,022,336 | A | 2/2000 | Zadno-Azizi et al. |
| 6,036,715 | A | 3/2000 | Yock |
| 6,050,972 | A | 4/2000 | Zadno-Azizi et al. |
| 6,080,170 | A | 6/2000 | Nash et al. |
| 6,123,698 | A | 9/2000 | Spears et al. |
| 6,135,991 | A | 10/2000 | Muni et al. |
| 6,145,859 | A | 11/2000 | Altherr et al. |
| 6,146,372 | A | 11/2000 | Leschinsky et al. |
| 6,159,195 | A | 12/2000 | Ha et al. |
| 6,161,695 | A | 12/2000 | Nicolais |
| 6,166,116 | A | 12/2000 | Sleeckx |
| 6,171,328 | B1 | 1/2001 | Addis |
| 6,176,844 | B1 * | 1/2001 | Lee ....................... 604/101.04 |
| 6,190,354 | B1 | 2/2001 | Sell et al. |
| 6,203,561 | B1 | 3/2001 | Ramee et al. |
| 6,217,567 | B1 | 4/2001 | Zadno-Azizi et al. |
| 6,231,588 | B1 | 5/2001 | Zadno-Azizi |
| 6,241,706 | B1 | 6/2001 | Leschinsky et al. |
| 6,245,008 | B1 | 6/2001 | Leschinsky et al. |
| 6,245,089 | B1 | 6/2001 | Daniel et al. |
| 6,248,121 | B1 | 6/2001 | Nobles |
| 6,251,093 | B1 | 6/2001 | Valley et al. |
| 6,475,185 | B1 | 11/2002 | Rauker et al. |
| 6,485,657 | B1 | 11/2002 | Funakoshi et al. |
| 6,494,314 | B1 | 12/2002 | Lamborne et al. |
| 6,511,472 | B1 * | 1/2003 | Hayman et al. ............. 604/533 |
| 6,544,276 | B1 | 4/2003 | Azizi |
| 6,554,794 | B1 * | 4/2003 | Mueller et al. ........... 604/95.04 |
| 6,786,492 | B2 | 9/2004 | Brandenburger |
| 6,902,535 | B2 | 6/2005 | Eberhart et al. |
| 6,927,063 | B2 | 8/2005 | Moreton et al. |
| 6,932,828 | B2 | 8/2005 | Bonnette et al. |
| 6,942,678 | B2 | 9/2005 | Bonnette et al. |
| 7,004,914 | B2 | 2/2006 | Eberhart et al. |
| 7,169,161 | B2 | 1/2007 | Bonnette et al. |
| 7,219,799 | B2 | 5/2007 | Bonnette et al. |
| 7,220,243 | B2 | 5/2007 | Bonnette et al. |
| 7,226,433 | B2 | 6/2007 | Bonnette et al. |
| 7,334,681 | B2 | 2/2008 | Bonnette et al. |
| 2001/0014821 | A1 | 8/2001 | Juman et al. |
| 2001/0016704 | A1 | 8/2001 | Zadno-Azizi et al. |
| 2002/0096521 | A1 | 7/2002 | Cardarelli |
| 2003/0088194 | A1 * | 5/2003 | Bonnette et al. ............ 600/585 |
| 2003/0088262 | A1 | 5/2003 | Bonnette et al. |
| 2003/0088263 | A1 | 5/2003 | Bonnette et al. |
| 2003/0208134 | A1 | 11/2003 | Secrest et al. |
| 2004/0031721 | A1 | 2/2004 | Mann |
| 2004/0039304 | A1 | 2/2004 | Connors, III et al. |
| 2004/0039306 | A1 | 2/2004 | Eberhart et al. |
| 2004/0050740 | A1 | 3/2004 | Lewis |
| 2005/0020998 | A1 | 1/2005 | Bonnette et al. |
| 2005/0182437 | A1 | 8/2005 | Bonnette et al. |
| 2006/0064071 | A1 | 3/2006 | Bonnette et al. |
| 2007/0060878 | A1 | 3/2007 | Bonnette |
| 2007/0060881 | A1 | 3/2007 | Bonnette et al. |
| 2008/0097294 | A1 | 4/2008 | Prather et al. |

FOREIGN PATENT DOCUMENTS

DE          10107631          9/2002

OTHER PUBLICATIONS

Material Data Sheet for Dow Calibre 2081 Polycarbonate Revealing the Color Stability, Dec. 12, 2004, Dow Chemicals.
International Search Report issued in related PCT application PCT/US05/41410.
International Search Report issued in related PCT application PCT/US02/35633.
International Search Report issued in related PCT application PCT/US05/14643.
International Search Report issued in related PCT application PCT/US05/14644.
International Search Report issued in related PCT application PCT/US06/33428.
International Search Report issued in related PCT application PCT/US07/22023.
Aegis Vortex System by Kensey Nash, www.bioexchange.com (undated).

\* cited by examiner

GAS INFLATION/EVACUATION SYSTEM INCORPORATING A MULTIPLE ELEMENT VALVED GUIDEWIRE ASSEMBLY HAVING AN OCCLUSIVE DEVICE

CROSS REFERENCES TO RELATED APPLICATIONS

None.

BACKGROUND OF THE INVENTION

1. Field of the Invention

The present invention relates generally to the field of vascular medical devices. More specifically, the present invention relates to a gas inflation/evacuation system incorporating a multiple element valved guidewire assembly having an occlusive device for selectively, rapidly and repeatedly inflating and deflating an occlusive balloon and for sealing the proximal end of a guidewire tube during a vascular procedure where the invention is incorporated for unencumbered hubless use as a guidewire with inflated occlusive balloon without any protruding features upon which thrombectomy catheters or other devices may align for thrombectomy or other procedures.

2. Description of the Prior Art

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of nonsurgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320,604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard nonsurgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520,645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice, such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons as well as most guidewire occlusive balloons utilize a liquid fluid such as saline or saline mixed with a radiopaque marker for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternative embodiments in U.S. Pat. No. 6,217,567. The only suggestion for how the guidewire of the alternative embodiment is sealed is a valve type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid filled occlusive balloons can remain in place too long and take too long to deflate, increasing the risk of damages downstream of the occlusion. Occlusive filters are designed to address this problem, but suffer from blockage problems and can be complicated to deploy and retrieve and may allow small embolic particles to migrate downstream. Existing gas-filled occlusive balloons solve some of the problems of liquid filled occlusive balloons, but typically have utilized complicated valve and connection arrangements. It would be desirable to provide for an occlusive device that was effective, simple, quick to deploy and deflate, and that could overcome the limitations of the existing approaches.

Some of these problems have been previously addressed in three commonly owned and assigned co-pending applications, which are hereby incorporated by reference herein: U.S. patent application Ser. No. 10/838,464, filed Apr. 29, 2004, entitled "Gas Inflation/Evacuation System and Sealing System for Guidewire Assembly Having Occlusive Device," which is a continuation-in-part of patent application Ser. No. 10/012,903, filed Nov. 6, 2001, entitled "Guidewire Occlusion System Utilizing Repeatably Inflatable Gas-Filled Occlusive Device," U.S. patent application Ser. No. 10/012,891, filed Nov. 6, 2001, entitled "Guidewire Assembly Having Occlusive Device and Repeatably Crimpable Proximal End," U.S. patent application Ser. No. 10/007,788, filed Nov. 6, 2001, entitled "Gas Inflation/Evacuation System and Sealing System for Guidewire Assembly Having Occlusive Device," and U.S. patent application Ser. No. 10/455,096, filed Jun. 6, 2003, entitled "Thrombectomy Device With Self-Sealing Hemostasis Valve," all of which are hereby incorporated herein by reference.

SUMMARY OF THE INVENTION

Disclosed herein is a gas inflation/evacuation system incorporating a multiple element valved guidewire assembly having an occlusive device. The gas inflation/evacuation system incorporating a multiple element valved guidewire assembly having an occlusive device includes a manifold assembly removably connectible to a multiple element valved guidewire assembly having an occlusive device, and in addition thereto includes syringe means operated in cooperation with the manifold assembly for selectively evacuating the multiple element valved guidewire assembly and syringe means operated in cooperation with the manifold assembly for introducing a biocompatible gas under pressure into the multiple element valved guidewire assembly to selectively inflate the occlusive device, such as an occlusive balloon, a plurality of times. The multiple element valved guidewire assembly is inserted and maneuvered within the manifold assembly to position a controllable valve therewithin for inflational and deflational control of the occlusive balloon. The multiple element valved guidewire assembly can be removed from influence of the manifold assembly subsequent to occlusive balloon inflation to serve as a stand-alone guidewire while providing occlusive protection within a blood vessel.

An embodiment set forth herein comprises a manifold assembly removably connectible to the multiple element valved guidewire assembly. The multiple element valved guidewire assembly includes a braided polyimide guidewire tube which defines a lumen, where the distal end of the braided polyimide guidewire tube includes an occlusive balloon, inflation orifices, a flexible distally located tip and a proximal end which includes an internally located seal. Also included as a part of the multiple element valved guidewire assembly is a one-piece flexible sealing rod having a reduced radius support extension extending therefrom, such being a part of the multiple element valved guidewire assembly and being slidably accommodated by the braided polyimide guidewire tube. More specifically, the sealing rod is intimately and slidingly accommodated by the seal internal to the proximal end of the braided polyimide guidewire tube to either seal or unseal the lumen leading to the occlusive balloon when inflating or deflating the occlusive balloon. Such an arrangement comprises a valve at the proximal end of the braided polyimide guidewire tube incorporating interaction of a portion of the multiple element valved guidewire assembly sealing rod. The reduced radius support extension extends along the lumen of the braided polyimide guidewire tube to add a degree of stiffness to the braided polyimide guidewire tube, thereby adding to the pushability of the multiple element valved guidewire assembly through the vasculature.

The manifold assembly removably receives the multiple element valved guidewire assembly. Multiple resilient seals are incorporated within the manifold assembly to seal against the elements of the multiple element valved guidewire assembly and to seal about the needles of the evacuation and inflation syringes. The valve of the multiple element valved guidewire assembly is accommodated and sealed within the manifold assembly and opened or closed during phases of inflation and deflation in coordinated operation of the evacuation and inflation syringes. Operation of the invention involves placement of the multiple element valved guidewire assembly into the vasculature to position a deflated occlusive balloon beyond a buildup of thrombus, plague, lesions or other foreign material buildup followed by the inflation of the occlusive balloon therein and then by removal of the manifold assembly from the multiple element valved guidewire assembly, thereby leaving in place a guidewire tube having an inflated occlusive balloon and a guidewire tube over which thrombectomy catheters or other devices may track for the purpose of thrombectomy or other procedures.

An advantage of the present invention is that the occlusive device can be repeatably inflated and deflated a plurality of times during a vascular procedure where the proximal end of the guidewire tube is alternately free of mechanical connections and obstructions and, therefore, the guidewire tube can function as a conventional exchange guidewire for one or more over-the-wire catheters. Alternatively, the guidewire tube can be shorter in length for use with rapid exchange catheter systems. Unlike operation of existing liquid filled occlusive devices, the present invention enables repeated and quick inflation and deflation which allows an operator to deploy the gas-filled occlusive device numerous times during a procedure for shorter periods of time, thereby reducing the risk of potential damage to downstream tissue. There are no complicated mechanical arrangements or complicated valve systems internal to the guidewire tube that increase the cost, complexity, and potential for failure of the system. Preferably, the gas inflation/evacuation system incorporating a multiple element valved guidewire assembly having an occlusive device constitutes a handheld apparatus. Each time a deflation of the occlusive device is desired in order to reestablish blood flow to the vessel downstream of the occlusive device, the sealing rod can be repositioned to open the valve to quickly deflate the occlusive device and after a determined period can be repositioned to repeat the inflation procedure again. Multiple inflations, evacuations and deflations can be performed as required.

One significant aspect and feature of the present invention is the provision of a multiple element valved guidewire, a manifold assembly, an evacuation syringe and an inflation syringe.

Another significant aspect and feature of the present invention is a removably attached manifold assembly which is accommodated by a multiple element valved guidewire assembly.

Another significant aspect and feature of the present invention is the provision for repeatable inflation and deflation of an occlusive balloon multiple times.

Another significant aspect and feature of the present invention is the use of a multiple element valved guidewire assembly which, subsequent to inflation of an occlusive balloon, can removed from influence of a manifold assembly to serve as a guidewire for accommodation of various devices.

Another significant aspect and feature of the present invention is a positionable valve in a multiple element valved guidewire assembly incorporated for selective supplying of inflational medium from an inflation syringe and for selective pressurization of various components of the invention or for selective evacuation thereof by the use of an evacuation syringe.

Another significant aspect and feature of the present invention is a multiple element valved guidewire assembly having structure including a sealing rod which interacts with a seal located proximally in a guidewire tube to constitute a valve where the closing or opening of the valve is accomplished by longitudinal movement of the sealing rod.

Yet another significant aspect and feature of the present invention is a guidewire tube and a sealing rod which together serve as a guidewire.

Another significant aspect and feature of the present invention is the incorporation of an evacuation syringe which cooperatively interacts to evacuate a multiple element valved guidewire assembly and a manifold assembly.

Another significant aspect and feature of the present invention is the incorporation of an inflation syringe which cooperatively interacts to pressurize a guidewire tube in order to inflate an occlusive balloon.

Another significant aspect and feature of the present invention is the use of a sealing rod having a support extension extending therefrom into a braided polyimide guidewire tube, whereby the support extension lends support to the braided polyimide guidewire tube and enhances pushability and deliverability of the braided polyimide guidewire tube through the vasculature.

Another significant aspect and feature of the present invention is the incorporation of a check valve in an evacuation syringe to prevent air injection.

Another significant aspect and feature of the present invention is the incorporation of a check valve in an inflation syringe to prevent air injection.

Still another significant aspect and feature of the present invention is the use of self and automatic sealing resilient seals or hemostatic valves in sealing relationships with elongated elements of a multiple element valved guidewire assembly passing therethrough.

Another significant aspect and feature of the present invention is a balloon on a commonly used and sized guidewire tube which gives the physician many options in using such a device to control the environment within a blood vessel while other procedures can take place more safely and effectively. Furthermore, having the device sealable or hubless facilitates complete freedom for use as a primary guidewire with the option of inflating an occlusive balloon for containment or mechanical usage.

Another significant aspect and feature of the present invention is a hubless guidewire tube which is provided with an occlusive balloon that can be used as a distal protection device.

Another significant aspect and feature of the present invention is a hubless guidewire tube having an occlusive balloon, the hubless guidewire tube with occlusive balloon being useful during embolectomy.

Another significant aspect and feature of the present invention is a hubless guidewire tube having an occlusive balloon, the hubless guidewire tube with occlusive balloon being useful in conjunction with an ablative device to remove clots, thrombus, plaque and the like from blood vessel walls.

Another significant aspect and feature of the present invention is a hubless guidewire tube having an occlusive balloon that can be inflated and used as a positioning tool to center other devices in a blood vessel.

Another significant aspect and feature of the present invention is an occlusive balloon on a hubless guidewire tube which can be used as an ordinary guidewire.

Another significant aspect and feature of the present invention is a hubless guidewire tube having an occlusive balloon that can be used as a containment device to minimize hemolysis or release of hemolytic blood components that may cause arrhythmia or organ damage.

Another significant aspect and feature of the present invention is a hubless guidewire tube having an occlusive balloon that can be used as a containment device for infused drugs or lysins to enhance their effect or improve safety.

Another significant aspect and feature of the present invention is a hubless guidewire tube having an occlusive balloon that can be used as one-half of an isolation system which contains materials more effectively where the other half could be a balloon on a device such as a thrombectomy catheter or a balloon on a guide catheter type device.

Another significant aspect and feature of the present invention is a hubless guidewire tube having an occlusive balloon which can be used as a containment device for infused drugs or lysins to enhance their effect or improve safety when injected via a specialized infusion catheter.

Another significant aspect and feature of the present invention is a hubless guidewire tube having an occlusive balloon which can be used as a containment device for infused drugs or lysins to enhance their effect or improve safety when injected via a high pressure thrombectomy catheter which employs cross stream technology power pulse spray with distal protection or containment therapy.

Another significant aspect and feature of the present invention is the incorporation of a pressure gauge to monitor inflation and evacuation procedures.

Having thus described embodiments of the present invention and enumerated significant aspects and features thereof, it is the principal object of the present invention to provide a gas inflation/evacuation system incorporating a multiple element valved guidewire assembly having an occlusive device.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
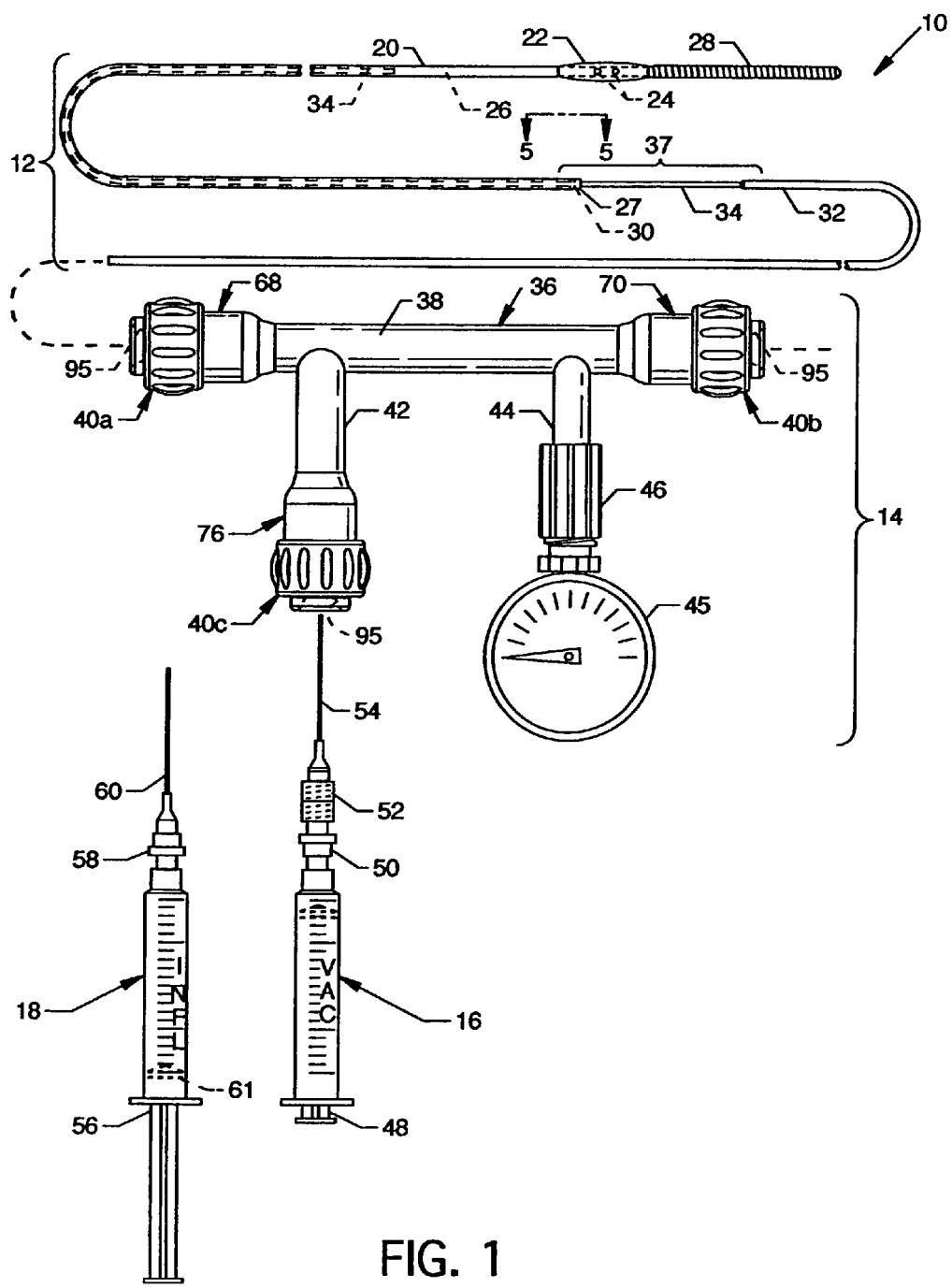
FIG. 1 is a view showing the overall outwardly visible structure of a gas inflation/evacuation system incorporating a multiple element valved guidewire assembly having an occlusive device, one embodiment of the present invention.

Referring to FIG. 1, the overall outwardly visible structure of the gas inflation/evacuation system incorporating a multiple element valved guidewire assembly having an occlusive device 10, one embodiment of the present invention, is now described. The gas inflation/evacuation system incorporating a multiple element valved guidewire assembly having an occlusive device 10 comprises a multiple element valved guidewire assembly 12, a manifold assembly 14, an evacuation syringe 16 and an inflation syringe 18.

The multiple element valved guidewire assembly 12 preferably includes, amongst other components described herein, a flexible guidewire tube 20 of braided polyimide, an occlusive device being an occlusive balloon 22 located at the distal end of guidewire tube 20, a plurality of inflation orifices 24 extending through the wall of the guidewire tube 20 in communication between a lumen 26 (FIGS. 5, 6 and 8) of the guidewire tube 20 and the occlusive balloon 22, a flexible tip 28 located distal to the occlusive balloon 22, and a seal 30 (FIGS. 5 and 6) of flexible compliant material located and fixed internally within the proximal end 27 of the guidewire tube 20.

Also included in the multiple element valved guidewire assembly 12 is a sealing rod 32 which is flexible and of a round cross section in close tolerance slidable and sealing fit with opening 29 (FIG. 5) provided by the seal 30. A flexible support extension 34 having a round cross section less than the round opening provided by the seal 30 and being continuous with the sealing rod 32 extends distally from the sealing rod 32. The support extension 34 and the sealing rod 32 are positionable within and through the seal 30 at the proximal end of the guidewire tube 20. The arrangement of components as just described also constitutes and makes possible the operation of a valve 37, as described in detail with reference to FIGS. 5 and 6. Additionally, the flexible support extension 34 extends into and through the seal 30 and further into and along a major portion of the lumen 26 of the guidewire tube 20 whereby the distal end of the support extension 34 comes in close proximity to the occlusive balloon 22 and can be positioned coaxially with the occlusive balloon 22 to lend support along and within the guidewire tube 20. When the valve 37 is closed, the sealing rod 32 is utilized in the same capacity as the guidewire tube 20 for accommodation of a thrombectomy catheter, i.e., the guidewire tube 20 and the sealing rod 32 together constitute a guidewire structure.

The manifold assembly 14 removably accommodates and attaches to and cooperates with the multiple element valved guidewire assembly 12 and cooperates with the evacuation syringe 16 and the inflation syringe 18 to provide for inflation and deflation of the occlusive balloon 22 at the distal end of the guidewire tube 20. Readily visible components of the manifold assembly 14 include a manifold 36 of tubular configuration, a manifold body 38, a plurality of similarly constructed hemostatic nuts including a proximal hemostatic nut 40a opposing a distal hemostatic nut 40b at the ends of the manifold body 38, and an inflation/evacuation branch hemostatic nut 40c located at the end of an inflation/evacuation branch 42. A pressure monitor branch 44 also extends from the manifold body 38 for connection to a pressure gauge 45 by an interceding connector 46. The evacuation syringe 16 includes a plunger 48, a check valve 50, a connector 52 and a needle 54 which preferably is a blunt needle. The inflation syringe 18 includes a plunger 56, a check valve 58 and a needle 60 which preferably is a blunt needle.

Figure 2:
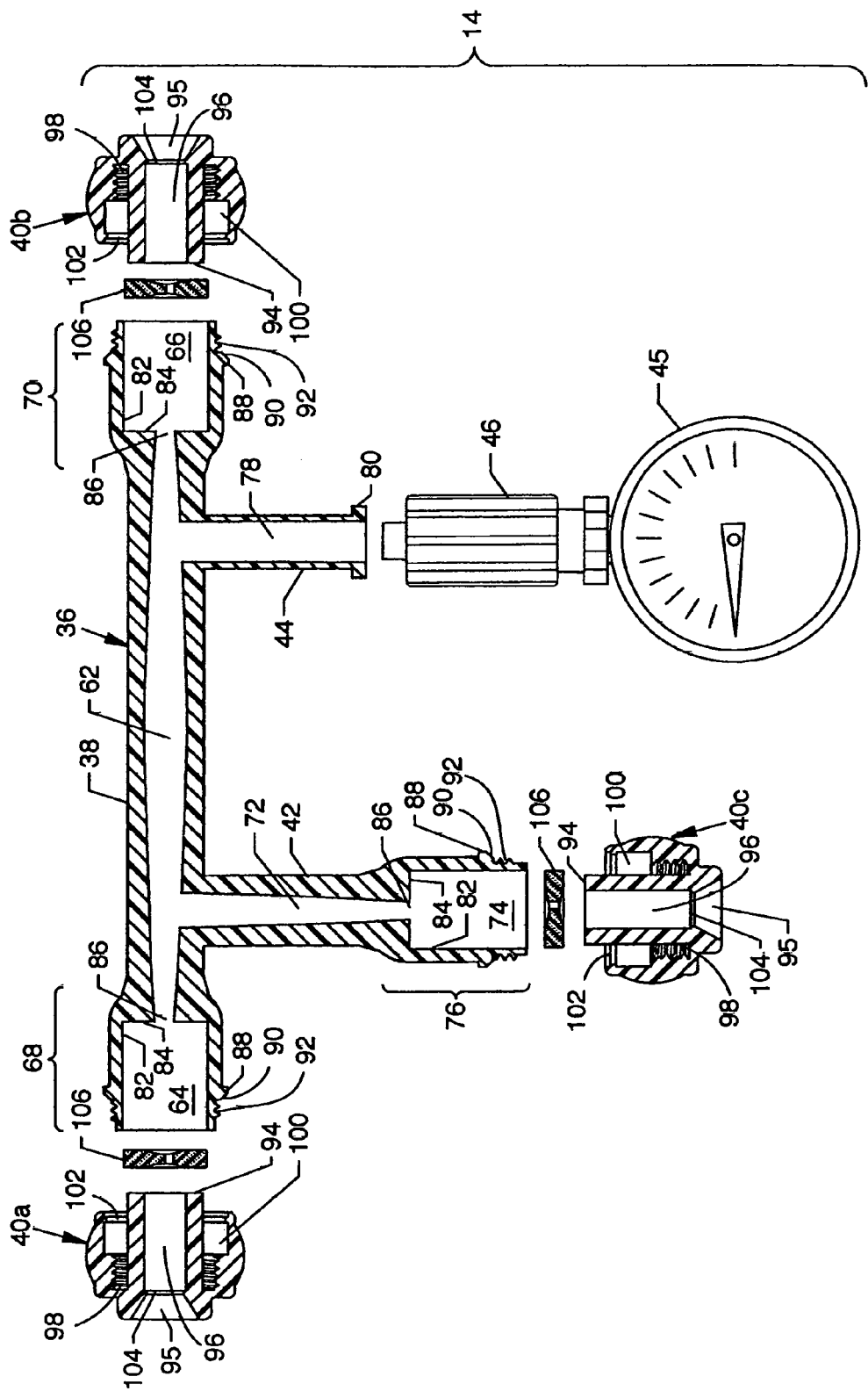
FIG. 2 is an exploded vertical cross section view through the manifold assembly.
Figure 3:
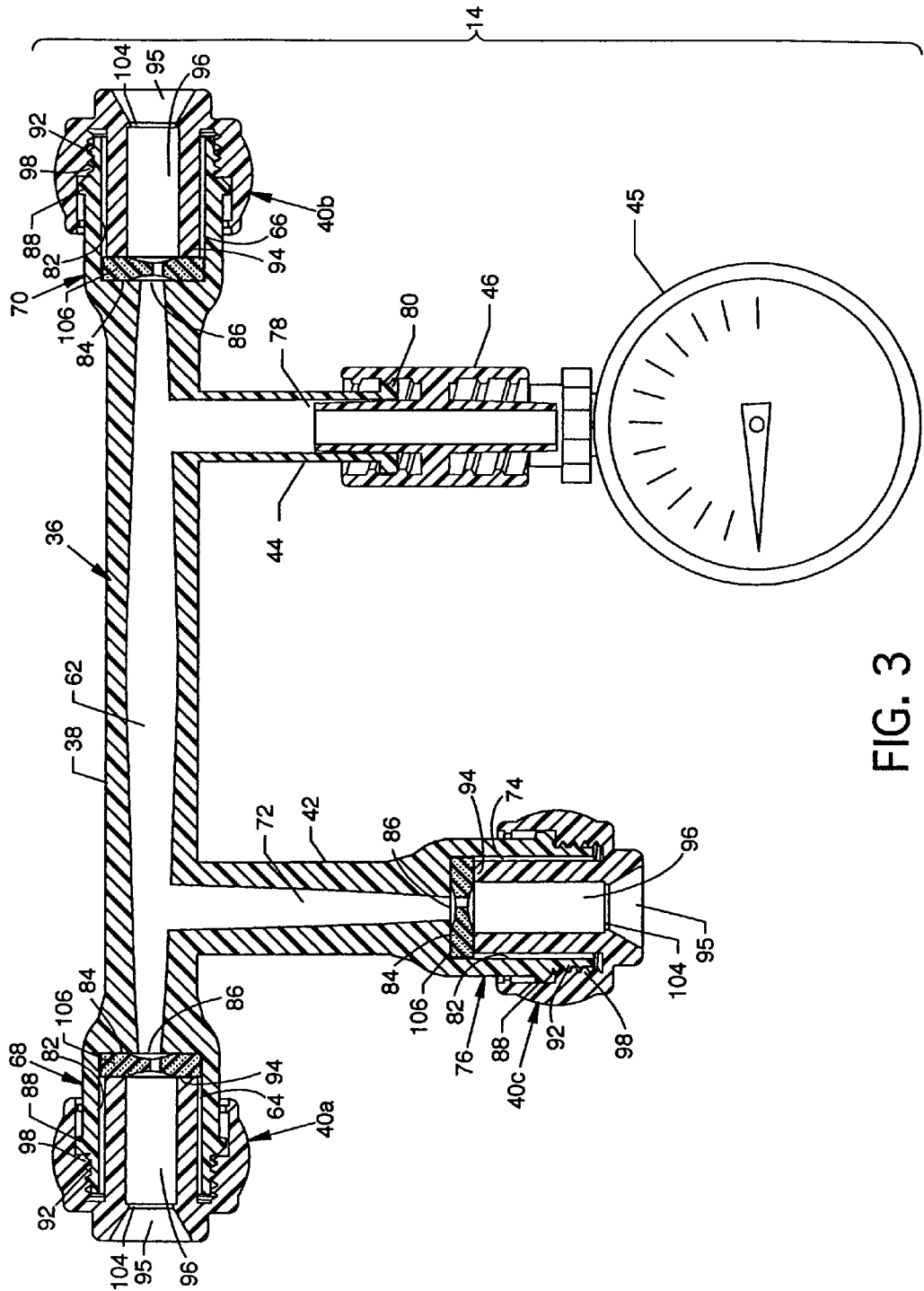
FIG. 3 is an assembled vertical cross section view through the manifold assembly.

FIGS. 2 and 3 are exploded and assembled vertical cross section views through the manifold assembly 14. The manifold assembly 14 includes structure for accommodation of the multiple element valved guidewire assembly 12 and for use of the evacuation and inflation syringes 16 and 18, respectively. Accordingly, the manifold body 38 of the manifold 36 includes connected and communicating passageways and cavities including a longitudinally oriented main passageway 62 being tapered in opposing directions extending through the central and tubular region of the manifold body 38 to communicate with opposed proximal and distal cavities 64 and 66, which preferably are cylindrical, located centrally in opposed proximal and distal cavity bodies 68 and 70 at the ends of the manifold body 38. An inflation/evacuation branch passageway 72, which is tapered, extends along the interior of the inflation/evacuation branch 42 between the main passageway 62 and an inflation/evacuation branch cavity 74, which preferably is cylindrical, located in an inflation/evacuation branch cavity body 76. A pressure monitor branch passageway 78 extends along the interior of the pressure monitor branch 44 between the main passageway 62 and a flange 80 for connection with the connector 46 and the pressure gauge 45.

The proximal cavity body 68, the distal cavity body 70, the inflation/evacuation branch cavity body 76 and accordingly, the associated proximal cavity 64, distal cavity 66, and the inflation/evacuation branch cavity 74, respectively, are fashioned similarly and as such contain like components and features identified by like reference numerals.

The proximal cavity 64, the distal cavity 66 and the inflation/evacuation branch cavity 74 are tubular, each including a cavity wall 82 and a planar surface 84 which is annular and circular and which intersects the cavity wall 82. An orifice 86 in each is located central to the surface 84 and is common either to the proximal cavity 64 and the main passageway 62, to the distal cavity 66 and the main passageway 62, or to the inflation/evacuation branch cavity 74 and the inflation/evacuation branch passageway 72.

The proximal cavity body 68, the distal cavity body 70, and the inflation/evacuation branch cavity body 76 each includes a ring 88 having an angled annular surface 90 located around and about the outwardly facing end of the cavity body, as well as external threads 92 being outwardly located with respect to the ring 88 and angled annular surface 90. The rings 88 and angled annular surfaces 90 provide in part for snap engagement of the manifold 36 to the proximal, distal and inflation/evacuation branch hemostatic nuts 40a, 40b and 40c, respectively.

Each of the hemostatic nuts 40a-40c includes a centrally located cylindrical boss 94 and a beveled entryway 95 leading to a passageway 96 extending through and in part defining the cylindrical boss 94. An annular cavity 100 is located about a portion of the cylindrical boss 94. Internal threads 98 of the hemostatic nuts 40a-40c and the annular cavities 100 of the hemostatic nuts 40a-40c accommodate the outwardly facing ends of the proximal and distal cavity bodies 68 and 70 and the inflation/evacuation branch cavity body 76, including the external threads 92 and the rings 88, respectively. A ring 102 is located inwardly of the internal threads 98 and about the inwardly facing interior region of each of the hemostatic nuts 40a-40c for the purpose of snap engagement with and beyond the rings 88 of the proximal cavity body 68, the distal cavity body 70, and the inflation/evacuation branch cavity body 76. The angled annular surface 90 adjacent to each ring 88 facilitates snap engagement of each ring 88 along and beyond a respective ring 102 of the hemostatic nuts 40a-40c. Such snap engagement (FIG. 3) loosely attaches the hemostatic nuts 40a-40c to the manifold 36 where the internal threads 98 of the hemostatic nuts 40a-40c can subsequently be made to engage the external threads 92 of the manifold 36, whereby the cylindrical bosses 94 are brought to bear against and bring pressure as required against self-sealing hemostatic valves 106, as shown in FIG. 3. The self-sealing hemostatic valves 106 are captured in the proximal cavity body 68, the distal cavity body 70 and the inflation/evacuation branch cavity body 76 by engagement of the hemostatic nuts 40a-40c to the proximal cavity 64, the distal cavity 66 or the inflation/evacuation branch cavity 74 of the manifold 36. Also included in the hemostatic nuts 40a-40c is an annular lip 104 which can be utilized for snap engagement of particular styles or types of introducers as required. Beneficial to the instant invention is the use of self-sealing hemostatic valves 106, the shape of which and the functions of which are described later in detail. The self-sealing hemostatic valves 106, which are slightly oversize with respect to the proximal cavity 64, the distal cavity 66 or the inflation/evacuation branch cavity 74, are aligned in and housed in such cavities at locations about the manifold 36.

Figure 4:
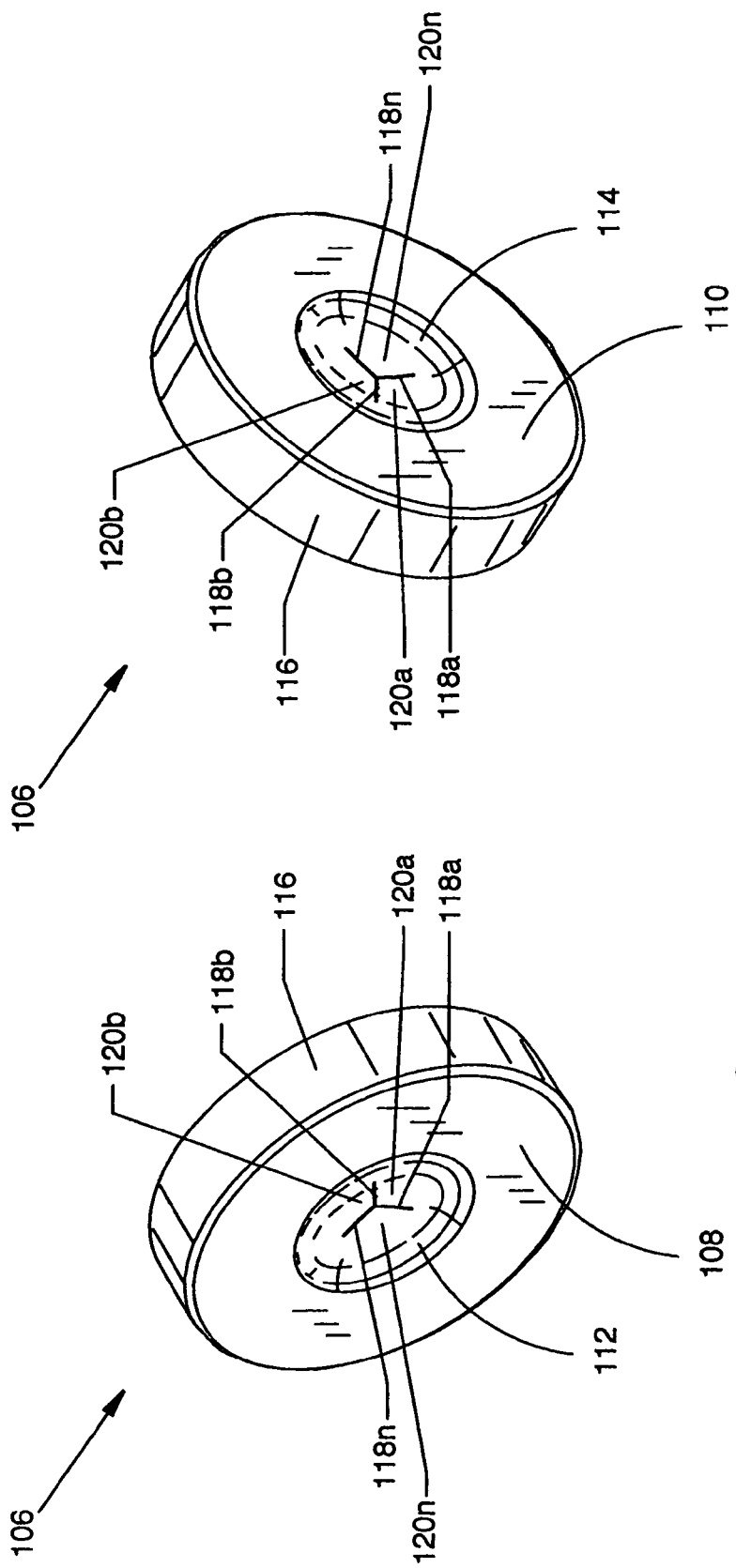
FIGS. 4a and 4b are isometric views of one of the self-sealing hemostatic valves which align in and which are housed in a proximal cavity, a distal cavity, and an inflation/evacuation branch cavity.

FIGS. 4*a* and 4*b* are isometric views of one of the self-sealing hemostatic valves 106 which align in and which are housed in the proximal cavity 64, the distal cavity 66, and the inflation/evacuation branch cavity 74 adjacent to and in contact with the planar surface 84 in such cavities at the ends of the manifold 36 and the end of the inflation/evacuation branch 42. FIG. 4*a* is a proximal view of the self-sealing hemostatic valve 106, and FIG. 4*b* is a distal view of such self-sealing hemostatic valve 106 associated with the proximal cavity 64. The self-sealing hemostatic valve 106 is compressible and multi-dimensional and sealingly expandable. The self-sealing hemostatic valve 106 is formed of medical grade silicone material and is symmetrically fashioned to include opposing mirror-like planar and circular-shaped faces 108 and 110 having opposing radiused recessed surfaces 112 and 114 extending therebetween and a circumferential edge 116 between the circular-shaped faces 108 and 110. The medical grade silicone material between the opposing radiused recessed surfaces 112 and 114 is increasingly thinner in a direction towards the center and is parted or otherwise separated to form a plurality of slits 118*a*-118*n*, each slit extending outwardly in radial fashion from the center of the self-sealing hemostatic valve 106 part of the distance along and between the radiused recessed surfaces 112 and 114, thus creating boundaries beneficial in defining lobes 120*a*-120*n*. That is to say, lobe 120*a* is located between slits 118*a* and 118*b*, lobe 120*b* is located between slits 118*b* and 118*n*, and lobe 120*n* is located between slits 118*n* and 118*a*. Adjacent lobes 120*a*-120*n* are in mutual contact along the slits 118*a*-118*n* to effect a seal from side-to-side of the self-sealing hemostatic valve 106. Although three lobes 120*a*-120*n* and three slits 118*a*-118*n* are shown, any number of each in correspondence can be utilized as desired and shall not be limiting to the scope of the invention. In the alternative, the silicone material of the self-sealing hemostatic valve 106 could be pierced between the recessed surfaces 112 and 114 to yet maintain a self-sealing quality. The self-sealing hemostatic valve 106 is preferably constructed of medical grade silicone or can be fashioned of other suitable flexible, pliable and resilient material which can conform to and about existing shapes or forms as required, such as to a guidewire or needle. The degree of flexibility of the lobes 120*a*-120*n*, is influenced by the thickness of the lobes 120*a*-120*n* each of which contains a portion of the radiused recessed surfaces 112 and 114. A guidewire, guidewire tube 20 or other round cross section device or member can pass between the inner tips of the lobes 120*a*-120*n* while maintaining a seal therebetween with the self-sealing hemostatic valve 106. Due to the similar geometrical configuration of the opposing faces and associated structure therebetween, the self-sealing hemostatic valve 106 can be inserted into a cavity without regard to orientation of the self-sealing hemostatic valve 106. The diameter of the self-sealing hemostatic valve 106 can be slightly larger than that of the cavities 64, 66 or 74 to provide for flexible, but snug, frictional engagement of the self-sealing hemostatic valve 106 within the cavities 64, 66 or 74, as well as providing for circumferential sealing of the self-sealing hemostatic valve 106 to the cavities 64, 66 or 74. Compressive force is transmitted into the self-sealing hemostatic valve 106 by tightening action of the proximal, distal and inflation/evacuation branch hemostatic nuts 40*a*-40*c* to compress the self-sealing hemostatic valve 106 around tubes, guidewires, or other elongated elements that pass through the self-sealing hemostatic valve 106. The self-sealing hemostatic valve 106 operates automatically; that is, when the self-sealing hemostatic valve 106 is penetrated by a tube, wire, or other elongated element inserted therethrough, the compressed self-sealing hemostatic valve 106 automatically causes sealing around the element that has penetrated it. U.S. patent application Ser. No. 10/455,096 filed Jun. 6, 2003, entitled "Thrombectomy Device With Self-Sealing Hemostasis Valve," which is incorporated herein by reference, includes a complete discussion of various structures and methods of incorporation of the self-sealing hemostatic valve 106.

Figure 5:
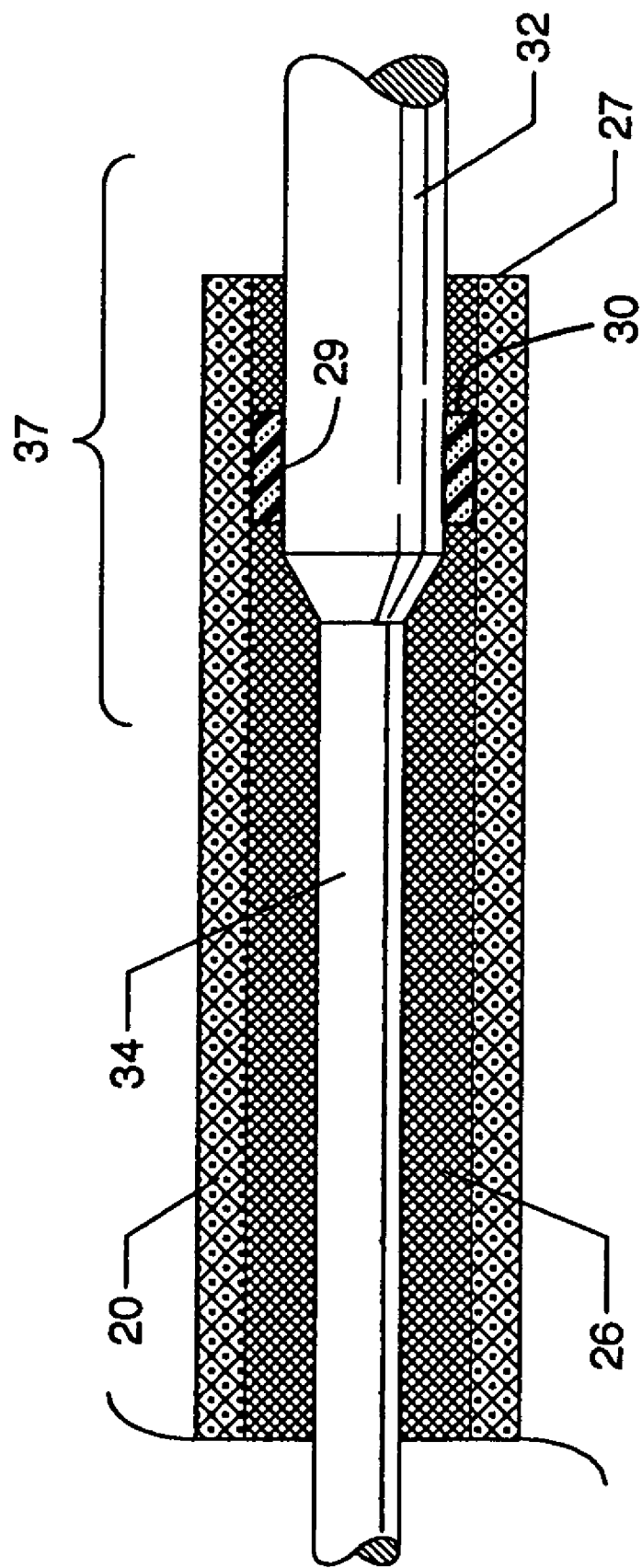
FIG. 5 is a cross section view of a valve along line 5-5 of FIG. 1 where the valve is in the closed position.

FIG. 5 is a cross section view of the valve 37 along line 5-5 of FIG. 1 where the valve 37 is in the closed position such as for maintaining pressure within the lumen 26 of the guidewire tube 20 to maintain the occlusive balloon 22 in an inflated state, as later described in the mode of operation. The opening 29 of the seal 30 forms a close tolerance interference slidable sealed fit with the exterior surface of the sealing rod 32 to seal the portion of the lumen 26 distal to the seal 30 from the portion of the lumen 26 proximal of the seal 30.

Figure 6:
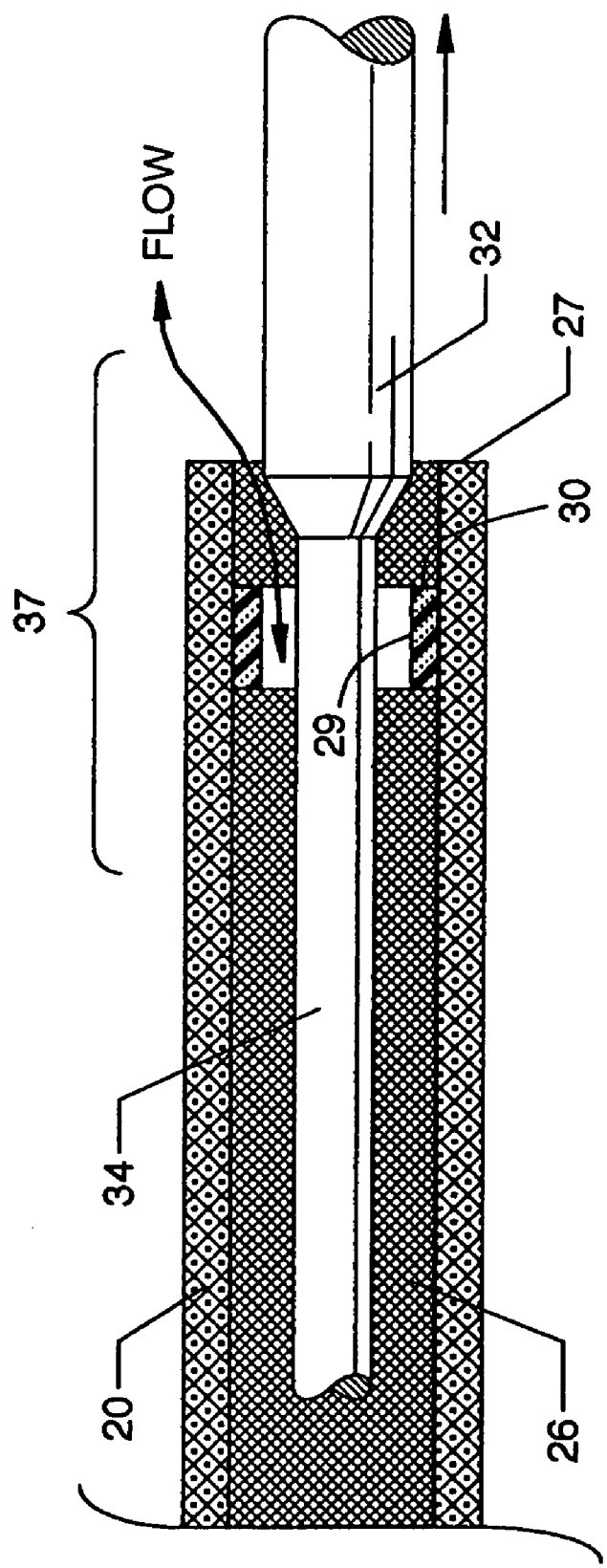
FIG. 6 is a cross section view of the valve along line 5-5 of FIG. 1 where the valve is in the open position.

FIG. 6 is a cross section view of the valve 37 along line 5-5 of FIG. 1 where the valve 37 is in the open position such as for relieving pressure within the lumen 26 of the guidewire tube 20 to allow collapsing of the occlusive balloon 22, as later described on the mode of operation. As illustrated, urging of the sealing rod 32 proximally removes the sealing rod 32 from the influence of the seal 30, thereby equalizing pressures distal and proximal of the seal 30.

Alternatively, any number of other alloys or polymer materials and attachment techniques could be used in the construction of the multiple element valved guidewire assembly 12 provided the materials offer the flexibility and torque characteristics required for a guidewire and the attachment techniques are sufficiently strong enough and capable of making an airtight seal. These materials include, but are not limited to, Ni—Ti, 17-7 stainless steel, _304 stainless steel, cobalt superalloys, or other polymer, braided or alloy materials. The attachment techniques for constructing multiple element valved guidewire assembly 12 include, but are not limited to, welding, mechanical fits, adhesives, sleeve arrangements, or any combination thereof.

The occlusive balloon 22 may be made of any number of polymer or rubber materials. Preferably, the occlusive balloon 22 is preinflated to prestretch it so that expansion is more linear with pressure. Preferably, the pressure supplied by the gas inflation/evacuation system incorporating a multiple element valved guidewire assembly having an occlusive device 10 is designed to stay well within the elastic limit of the occlusive balloon 22. A two-layer occlusive balloon arrangement, adding gas and/or liquid between balloon layers, may be used as an alternative to increase visibility of the distal end of the multiple element valved guidewire assembly 12 under fluoroscopy.

MODE OF OPERATION

The instant invention is generally used in the following manner where a patient is prepared for a common interventional procedure involving the ablative removal of thrombus, plaque, lesions and the like, for instance, via a femoral arterial access or other suitable vascular site. The distal end of the multiple element valved guidewire assembly 12 is inserted alone or through a pre-positioned sheath, a guide catheter or an introducer and is tracked to a preferred location distal to the buildup site. Subsequent to such positioning, the occlusive balloon 22 can be repeatedly inflated and deflated as required to controllingly and appropriately allow blood flow, to actively function as an occlusive device. The multiple element valved guidewire assembly 12 can serve as a guidewire for loading of and for use with ablation catheter devices, for placement of stents, or for other procedures. Subsequent to placement of the multiple element valved guidewire assembly 12 in the vasculature, the proximal end of the sealing rod 32 is loaded into the proximal hemostatic nut 40a of the manifold assembly 14 and thence through the distal hemostatic nut 40b and advanced until the valve 37 is contained therebetween in the main passageway 62 of the manifold 36. Then vacuum is utilized by operation and subsequent removal of the evacuation syringe 16 to purge the manifold assembly 14 and the multiple element valved guidewire assembly 12 of air or other gaseous substances. Then metered biocompatible, highly blood soluble gas, such as $CO_2$, helium, or other biocompatible gas, is introduced into the interior of the manifold 36 and through the open valve 37 by action of the inflation syringe 18 to inflate the occlusive balloon 22 to a desired size. The sealing rod 32 is then activated to close the valve 37. The manifold assembly 14 then is removed from the multiple element valved guidewire assembly 12 leaving the multiple element valved guidewire assembly 12 including the inflated occlusive balloon 22 and the guidewire structure composed of the guidewire tube 20 and sealing rod 32 in place at the vascular site without the manifold (hubless) to be used with any other compatible interventional device, such as a thrombectomy catheter or a stent, in the manner desired. Thus, having a basic understanding of the present invention, the mode and method of operation and other features of the instant invention are now described with particular reference to FIGS. 7, 8 and 9 and understood reference to other illustrations where FIGS. 7, 8 and 9 are described below.

Figure 7:
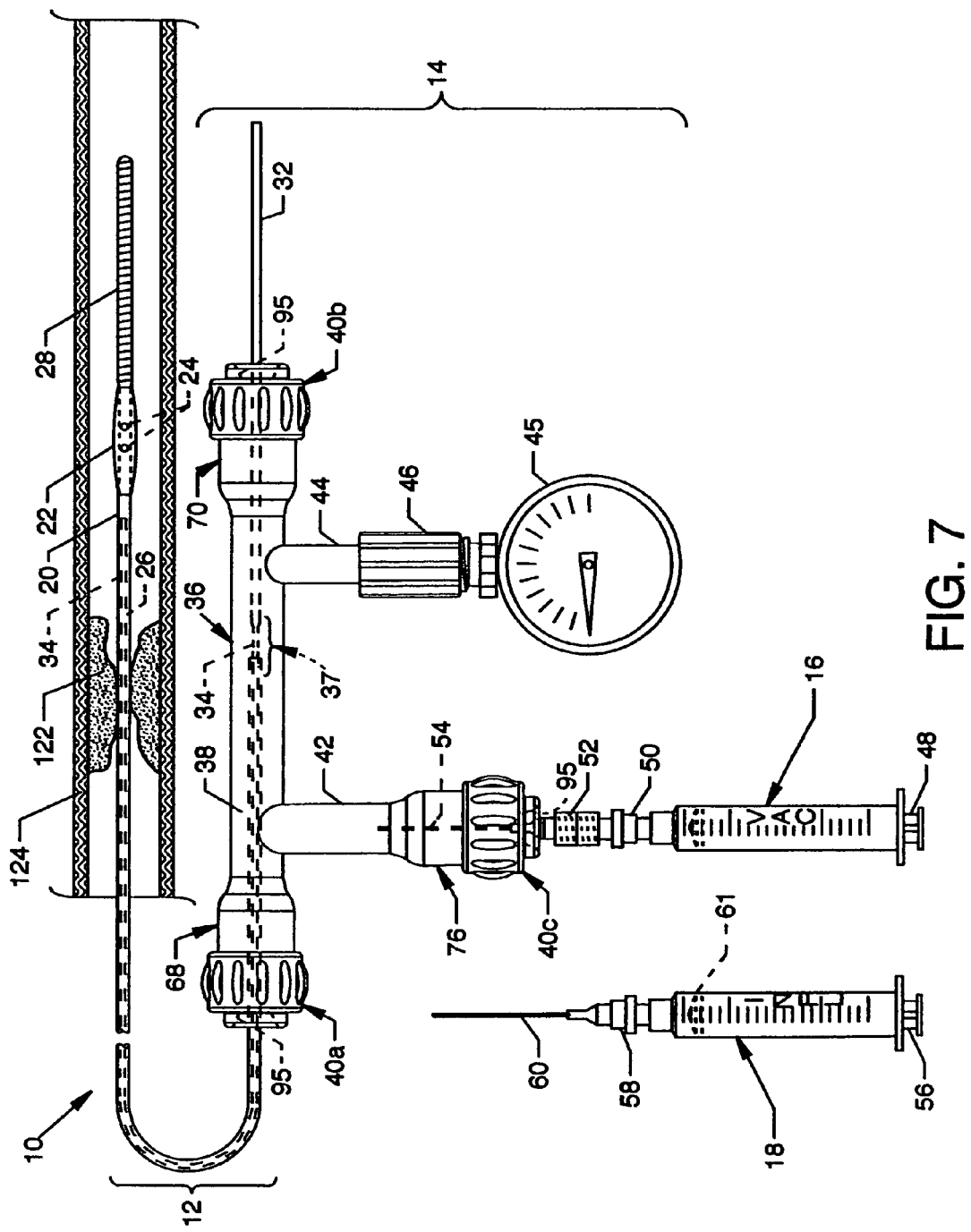
FIG. 7 is a view of the gas inflation/evacuation system incorporating a multiple element valved guidewire assembly having an occlusive device in use within a blood vessel.

FIG. 7 is a view of the gas inflation/evacuation system incorporating a multiple element valved guidewire assembly having an occlusive device 10 in use within a blood vessel 124 having a buildup of thrombus, plaque, or lesions 122 (or other undesirable foreign material) where the flexible tip 28 and the occlusive balloon 22 have been advanced to a location distal of the thrombus, plaque, or lesions 122 within the blood vessel 124.

Figure 8:
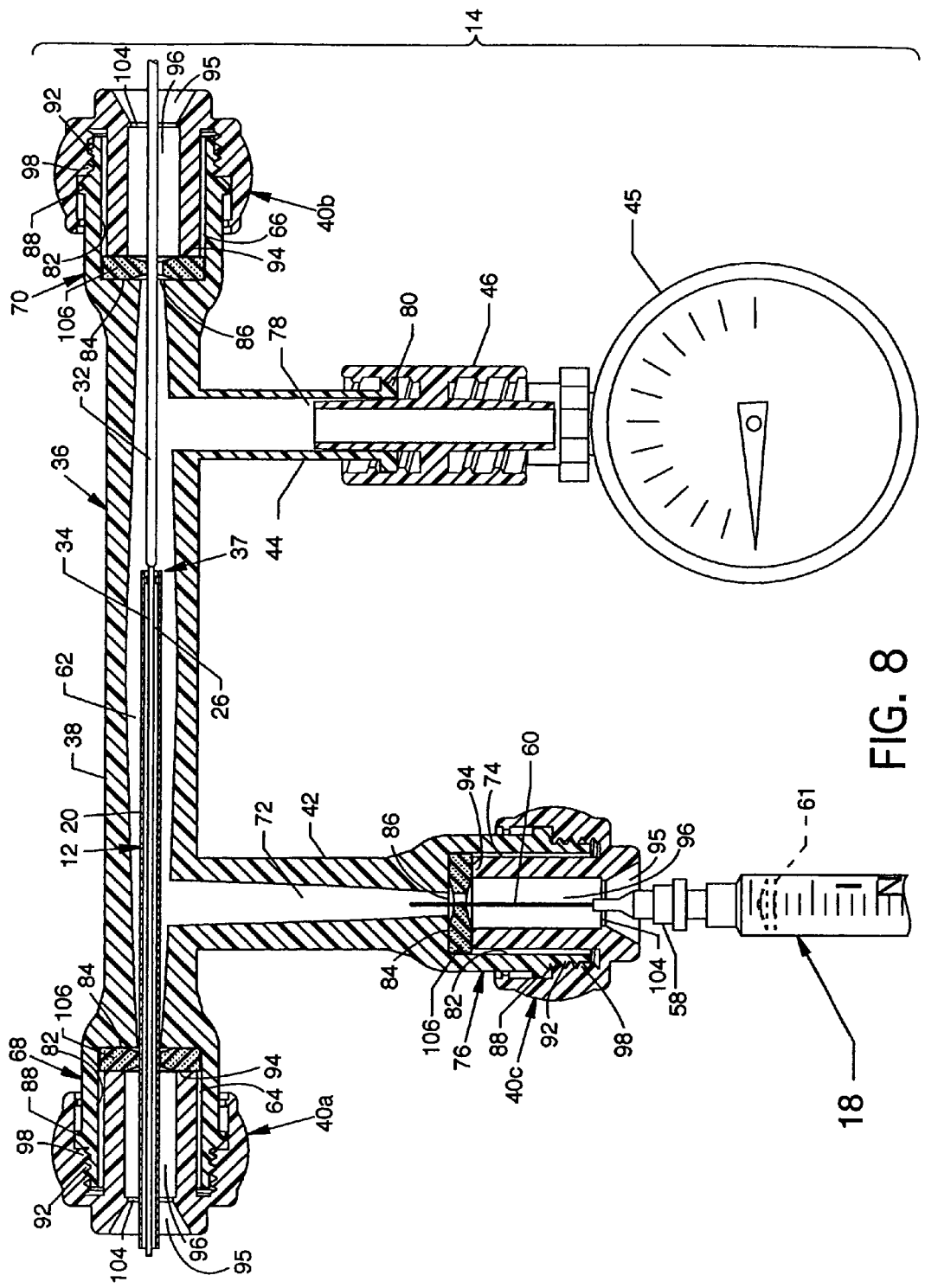
FIG. 8 is a cross section view like FIG. 3 but showing the valve of the multiple element valved guidewire assembly sealingly located in the main passageway of the manifold.

FIG. 8 is a cross section view like FIG. 3 but showing the valve 37 of the multiple element valved guidewire assembly 12 sealingly located in the main passageway 62 of the manifold 36.

Figure 9:
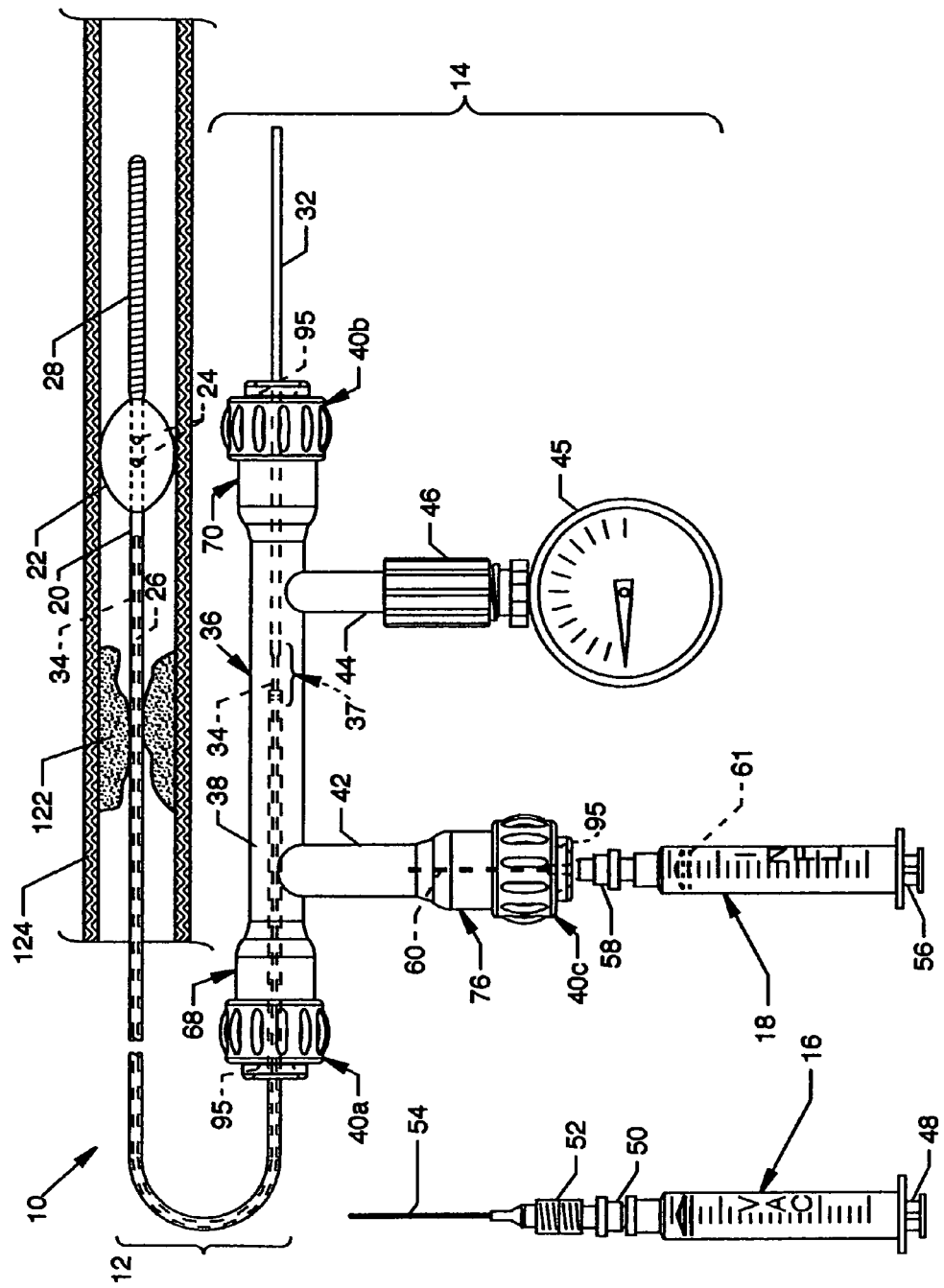
FIG. 9 is a view like FIG. 7 but showing the occlusive balloon inflated to occlude a blood vessel; and, FIG. 10, an alternative embodiment, is a view showing the overall outwardly visible structure of a gas inflation/evacuation system incorporating a multiple element valved guidewire assembly having an occlusive device using an attached vacuum syringe and an attached inflation syringe.

FIG. 9 is a view like FIG. 7 but showing the occlusive balloon 22 inflated to occlude the blood vessel 124. The method and manner of operation of the present invention is now set forth.

1. Prior to or subsequent to placement of the distal end of the multiple element valved guidewire assembly 12 into the vasculature, the proximal end of the multiple element valved guidewire assembly 12 (more specifically, the proximal end of the sealing rod 32) is inserted into the proximal hemostatic nut 40a to seal within the self-sealing hemostatic valve 106 therein and to pass into and through the main passageway 62 of the manifold body 38 until passing through and sealing within the self-sealing hemostatic valve 106 of the distal hemostatic nut 40b to position the valve 37 between the proximal and distal hemostatic nuts 40a and 40b in the main passageway 62. The valve 37 within the main passageway 62 is in a location to selectively allow communication between the lumen 26 and attached occlusive balloon 22 of the guidewire tube 20 with the main passageway 62, with the inflation/evacuation branch passageway 72 of the inflation/evacuation branch 42, and with the pressure monitor branch passageway 78 of the pressure monitor branch 44. The self-sealing hemostatic valves 106 in the proximal cavity 64, in the distal cavity 66, and in the inflation/evacuation branch cavity 74 seal the ends of the main passageway 62 and the end of the inflation/evacuation branch passageway 72, respectively, to provide for a sealed but accessible interior of the manifold assembly 14.

2. The needle 54 of the evacuation syringe 16 is inserted through the self-sealing hemostatic valve 106 associated with the inflation/evacuation branch hemostatic nut 40c, and the plunger 48 of the evacuation syringe 16 is withdrawn to evacuate the main passageway 62, the inflation/evacuation branch passageway 72 and the pressure monitor branch passageway 78 of the manifold assembly 14 where the vacuum (or pressure) is observed on the pressure gauge 45. Accordingly, when the valve 37 is in the open position by positioning of the sealing rod 32, such as shown in FIG. 6, the lumen 26 of the guidewire tube 20 and the occlusive balloon 22 are in common communication with main passageway 62 of the manifold body 38 and also subjected to the applied vacuum and are also evacuated. Such evacuation also minimizes the profile of the occlusive balloon 22. The check valve 50 of the evacuation syringe 16 functions to stabilize and maintain the outwardly advanced position of the plunger 48 during evacuation. The evacuation syringe 16 is then withdrawn from engagement with the automatically self-sealing hemostatic valve 106 associated with the inflation/evacuation branch hemostatic nut 40c leaving the manifold assembly 14 and the multiple element valved guidewire assembly 12 in a sealed and evacuated state.

3. The needle 60 of the inflation syringe 18, is then inserted through the self-sealing hemostatic valve 106 associated with the inflation/evacuation branch hemostatic nut 40c, and the plunger 56 of the inflation syringe 18 is depressed to dispel and urge a suitable quantity of biocompatible inflation medium, preferably a gaseous medium, from the interior of the inflation syringe 18 into the interior of the manifold 36 and thence through the open valve 37 and through lumen 26 of the guidewire tube 20 to inflate the occlusive balloon 22 while observing the pressure gauge 45 where appropriately used volumes can be observed by viewing a displaceable piston 61 located in the inflation syringe 18. Preferably, the inflation medium is a gas such as carbon dioxide or helium which are biocompatible and which dissolve easily in blood or which will not form a gas embolus. The check valve 58 of the inflation syringe 18 functions to stabilize and maintain the inwardly advanced position of the plunger 56 during inflation.

4. When suitable inflation of the occlusive balloon 22 is attained, the valve 37 is then closed by urging the sealing rod 32 in a distal direction to achieve closure of the valve 37, as depicted in FIG. 5, wherein the multiple element valved guidewire assembly 12 maintains pressure within the lumen 26 and within the occlusive balloon 22, and wherein the occlusive balloon 22 maintains an inflated state in intimate and sealing contact with the interior of the blood vessel 124, as shown in FIG. 9.

5. Upon desired inflation of the occlusive balloon 22 and after ensuring the closed position of the valve 37, the inflation syringe 18 can be withdrawn from the automatically self-sealing hemostatic valve 106 associated with the hemostatic nut 40c. The manifold assembly 14 is then disengaged in a proximal direction from the multiple element valved guidewire assembly 12 leaving the pressurized multiple element valved guidewire assembly 12 undisturbed in the vascular site, i.e., the inflated occlusive balloon 22 is left in place in the blood vessel 124 with the guidewire tube 20, whereupon the guidewire tube 20 can function as a guidewire.

6. The guidewire tube 20 along with the sealing rod 32 of the multiple element valved guidewire assembly 12 is then utilized unitarily for guidance of other devices, such as catheters, thrombectomy catheters, stents, and the like, to a vascular site proximal of the inflated occlusive balloon 22.

7. An ablation or other procedure is performed for a time period consistent with the desired maximum length for blockage of the particular vessel after which the valve 37 may be opened by repositioning the sealing rod 32, such as shown in FIG. 6, to equalize internal pressure with atmospheric pressure to rapidly deflate the occlusive balloon 22, thereby reestablishing blood flow within the vessel 124. The occlusive balloon 22 can be re-inflated and the valve 37 reclosed to continue with thrombus removal or to initiate another procedure. Depending upon the nature of the procedure, the multiple element valved guidewire assembly 12 may be removed from the vessel or left in place. Preferably, an evacuation of any plaque material or other debris dislodged by the therapy is accomplished before deflation of the occlusive balloon 22.

8. Removal of the multiple element valved guidewire assembly 12 from the vasculature is accomplished by repositioning of the sealing rod 32 to open the valve 37 to atmosphere to collapse the occlusive balloon 22 for withdrawal. A further reduction of the physical cross section of the occlusive balloon 22 for minimum profile removal of the multiple element valved guidewire assembly 12, i.e., the occlusive balloon 22, can be accomplished by reinserting the proximal end of the sealing rod 32 of the multiple element valved guidewire assembly 12 into the manifold assembly 14, if not already present, and accomplishing the evacuation steps outlined in steps 1 and 2 above.

9. Further and repeated use of the invention can be accomplished by repetition of steps 1 through 7 utilizing additional inflation syringes 18 as required.

Figure 10:
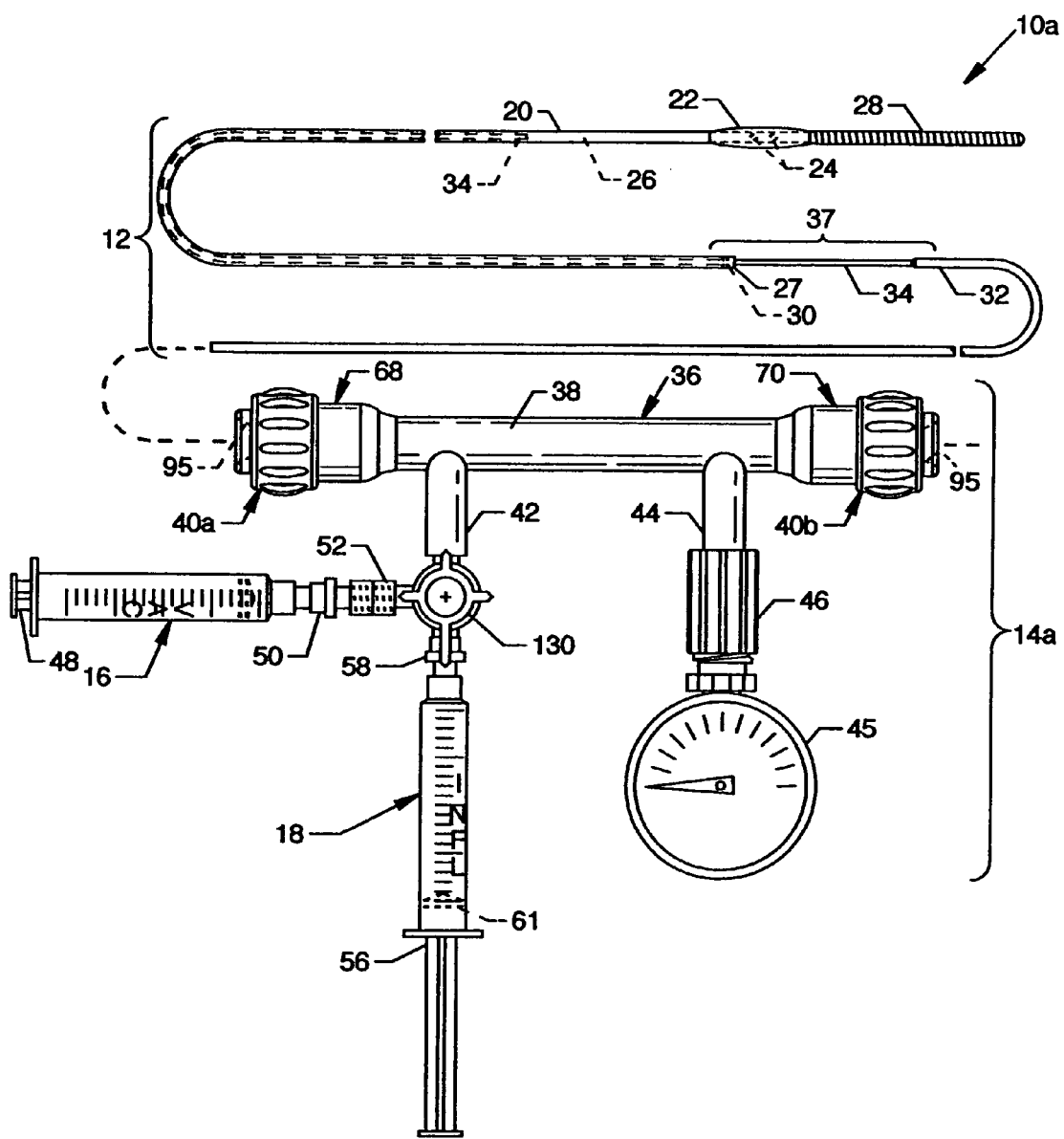

FIG. 10, an alternative embodiment, is a view showing the overall outwardly visible structure of a gas inflation/evacuation system incorporating a multiple element valved guidewire assembly having an occlusive device 10a incorporating many of the principles and components of the gas inflation/evacuation system incorporating a multiple element valved guidewire assembly having an occlusive device 10. In this alternative embodiment, the evacuation syringe 16 and the inflation syringe 18 are threadingly engaged to a manifold assembly 14a via an intermediate positionable valve 130, thus negating the use of the needles 54 and 60 previously shown. The use of the inflation/evacuation branch cavity body 76 is not required, nor is the associated self-sealing hemostatic valve 106, as sealing is accomplished by the positionable valve 130. Accordingly, the inflation/evacuation branch hemostatic nut 40c and associated self-sealing hemostatic valve 106 are not incorporated therein. Operation of the gas inflation/evacuation system incorporating a multiple element valved guidewire assembly having an occlusive device 10a is much the same as previously described, but differs in that the positionable valve 130 determines whether the evacuation syringe 16 or the inflation syringe 18 is in communication with the main passageway 62 through the inflation/evacuation branch 42.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

Various modifications can be made to the present invention without departing from the apparent scope hereof.

PARTS LIST 10 gas inflation/evacuation system incorporating a multiple element valved guidewire assembly having an occlusive device
10a gas inflation/evacuation system incorporating a multiple element valved guidewire assembly having an occlusive device
12 multiple element valved guidewire assembly
14 manifold assembly
14a manifold assembly
16 evacuation syringe
18 inflation syringe
20 guidewire tube
22 occlusive balloon
24 inflation orifice
26 lumen
27 proximal end
28 flexible tip
29 opening
30 seal
32 sealing rod
34 support extension
36 manifold
37 valve
38 manifold body
40a proximal hemostatic nut
40b distal hemostatic nut
40c inflation/evacuation branch hemostatic nut
42 inflation/evacuation branch
44 pressure monitor branch
45 pressure gauge
46 connector
48 plunger
50 check valve
52 connector
54 needle
56 plunger
58 check valve
60 needle
61 displaceable piston
62 main passageway
64 proximal cavity
66 distal cavity
68 proximal cavity body
70 distal cavity body
72 inflation/evacuation branch passageway
74 inflation/evacuation branch cavity
76 inflation/evacuation branch cavity body
78 pressure monitor branch passageway
80 flange
82 cavity wall
84 planar surface
86 orifice
88 ring
90 angled annular surface
92 external threads
94 cylindrical boss
95 beveled entryway
96 passageway
98 internal threads
100 annular cavity
102 ring
104 annular lip 106 self-sealing hemostatic valve
108 face
110 face
112 recessed surface
114 recessed surface
116 circumferential edge
118a-n slits
120a-n lobes
122 thrombus, plaque, or lesions
124 blood vessel
130 positionable valve It is claimed:

1. A gas inflation/evacuation system comprising:
 a. a multiple element valved guidewire assembly for enabling guidance and use of various intravascular devices, the multiple element valved guidewire assembly including:
  i. a guidewire tube having a proximal end and a distal end and defining a lumen therein, the guidewire tube being flexible and having an occlusive balloon near the distal end thereof and defining in a wall thereat at least one orifice in communication with the occlusive balloon to permit inflation and evacuation thereof;
  ii. a seal fixed internally within the proximal end of the guidewire tube; the seal defining an opening therein, and
  iii. a sealing rod and a support extension extending distally therefrom, the sealing rod having a cross section larger than that of the support extension, the support extension and the sealing rod being slidable within the lumen of the guidewire tube and within the opening of the seal disposed in the proximal end of the guidewire tube to form a flow valve thereat such that the flow valve is in (A) an open position when the sealing rod is slid proximally relative to and away from the opening and (B) in a closed position when the sealing rod is slid distally into the opening wherein the exterior surface of the sealing rod forms a sealed fit therein;
 b. a manifold assembly removably connectible to the multiple element valved guidewire assembly, the manifold assembly having a manifold body inclusive of a manifold, a first branch and a second branch such that:
  i. the manifold defines a main passageway wherein a hemostatic valve is sealingly disposed at each end thereof, the main passageway for permitting the proximal end of the guidewire tube to be removably inserted therein through the hemostatic valve at one end with the sealing rod thereof protruding from the hemostatic valve at the other end such that the flow valve is located within the main passageway between the hemostatic valves;
  ii. the first branch defines an inflation/evacuation passageway in communication with the main passageway; and
  iii. the second branch defines a pressure monitor passageway in communication with the main passageway, the pressure monitor passageway being adapted to enable a pressure gauge to be removably connectible thereto for monitoring pressure within the manifold assembly and, when the flow valve is situated in the main passageway and placed in the open position therein, within the guidewire tube and the occlusive balloon near the distal end thereof;
 c. an evacuation syringe being adapted for cooperation with the first branch of the manifold assembly for selectively withdrawing a biocompatible gas from the multiple element valved guidewire assembly so as to selectively evacuate the occlusive balloon a plurality of times; and,
 d. an inflation syringe being adapted for cooperation with the first branch of the manifold assembly for selectively introducing a biocompatible gas under pressure into the multiple element valved guidewire assembly so as to selectively inflate the occlusive balloon a plurality of times.

2. The gas inflation/evacuation system of claim 1, wherein the guidewire tube is made of braided polyimide; a flexible tip is located distal to the occlusive balloon; and, the seal comprises a flexible compliant material.

3. The gas inflation/evacuation system of claim 1, wherein the evacuation syringe includes a plunger, a check valve, a connector and a needle.

4. The gas inflation/evacuation system claim 3, wherein the needle of the evacuation syringe is blunt.

5. The gas inflation/evacuation system of claim 1, wherein at least one of the evacuation syringe and the inflation syringe includes a plunger, a check valve, and a needle.

6. The gas inflation/evacuation system of claim 5, wherein the needle is blunt.

7. The gas inflation/evacuation system of claim 1, wherein the hemostatic valves each include a hemostatic nut threadably connectible to the manifold body and snappingly engageable to the manifold body.

8. The gas inflation/evacuation system of claim 7, wherein the hemostatic valves are each self-sealing hemostatic valves, each being compressible and sealingly expandable.

9. The gas inflation/evacuation system of claim 8, wherein the hemostatic valves are formed of silicone material.

10. The gas inflation/evacuation system of claim 9, wherein the hemostatic valves are symmetrically fashioned and include mirror-like planar and circular-shaped faces having opposing radiused recessed surfaces increasingly thinner in a direction toward the center.

11. The gas inflation/evacuation system of claim 10, wherein the hemostatic valves each have a plurality of slits.

12. The gas inflation/evacuation system of claim 11, wherein the plurality of slits of the hemostatic valves extend outwardly in radial fashion from the center of the hemostatic valve thereby creating boundaries and defining lobes.

13. The gas inflation/evacuation system of claim 12, wherein the hemostatic valves have plural lobes defined by boundaries corresponding to slits, such that adjacent lobes have mutual contact along a slit and thereby effect a seal from side-to-side, thereby effecting a self-sealing hemostatic valve relationship to be formed on the manifold.

14. The gas inflation/evacuation system of claim 13, wherein the hemostatic valves each have three slits.

15. The gas inflation/evacuation system of claim 14, wherein the hemostatic valves are each self-sealing hemostatic valves, which can be modified in sealing properties by the hemostatic nut associated therewith.

16. The gas inflation/evacuation system of claim 1, wherein the occlusive balloon may be inflated or deflated when the flow valve is open and is maintained when the flow valve is closed.

17. The gas inflation/evacuation system of claim 1, wherein the occlusive balloon is formed of a material selected from polymer or rubber.

18. The gas inflation/evacuation system of claim 17, wherein the occlusive balloon has been prestretched to render expansion relatively linear with pressure.

19. The gas inflation/evacuation system of claim 1, wherein the distal end of the multiple element valved guidewire assembly is visible under fluoroscopy.

20. The gas inflation/evacuation system of claim 19, wherein the occlusive balloon is two-layer balloon with a fluoroscopy visible liquid employed between layers of the two-layer balloon.

21. A gas inflation/evacuation system comprising:
 (a) a guidewire assembly for enabling guidance and use of various intravascular devices, the guidewire assembly including:
  (i) a guidewire tube having a proximal end and a distal end and defining a lumen therein, the guidewire tube being flexible and having an occlusive balloon near the distal end thereof and defining in a wall thereat at least one orifice in communication with the occlusive balloon to permit inflation and evacuation thereof;
  (ii) a seal fixed internally within the proximal end of the guidewire tube; the seal defining an opening therein, and
  (iii) a sealing rod and a support extension extending distally therefrom, the sealing rod having a cross section larger than that of the support extension, the support extension and the sealing rod being slidable within the lumen of the guidewire tube and within the opening of the seal disposed in the proximal end thereof to form a flow valve thereat such that the flow valve is in (A) an open position when the sealing rod is slid proximally relative to and away from the opening and (B) in a closed position when the sealing rod is slid distally into the opening wherein the exterior surface of the sealing rod forms a sealed fit therein; and
 (b) a manifold assembly removably operable with the guidewire assembly, the manifold assembly having a manifold body inclusive of a manifold, a first branch and a second branch such that:
  (i) the manifold defines a main passageway wherein a hemostatic valve is sealingly disposed at each end thereof, the main passageway for permitting the proximal end of the guidewire tube to be removably inserted therein through the hemostatic valve at one end with the sealing rod thereof protruding from the hemostatic valve at the other end such that the flow valve is located within the main passageway between the hemostatic valves;
  (ii) the first branch defines an inflation/evacuation passageway in communication with the main passageway, the first branch being adapted for cooperation with (A) an evacuation syringe for selectively withdrawing a biocompatible gas from the guidewire assembly so as to selectively evacuate the occlusive balloon a plurality of times via the flow valve when in the open position and (B) an inflation syringe for selectively introducing a biocompatible gas under pressure into the guidewire assembly so as to selectively inflate the occlusive balloon a plurality of times via the flow valve when in the open position, the pressure within the occlusive balloon being maintainable when the flow valve is in the closed position; and
  (iii) the second branch defining a pressure monitor passageway in communication with the main passageway, the pressure monitor passageway being adapted to enable a pressure gauge to be removably connectible thereto for monitoring pressure within the manifold assembly and, when the flow valve is situated in the main passageway and placed in the open position therein, within the guidewire tube and the occlusive balloon near the distal end thereof.

22. The gas inflation/evacuation system of claim 21 wherein the manifold assembly further includes an intermediate positionable valve threadingly engaged to an end of the first branch through which the evacuation syringe and the inflation syringe are selectively enabled to communicate with the inflation/evacuation passageway of the manifold assembly.

23. A manifold assembly of a gas inflation/evacuation system for use with a intravascular device, the intravascular device having a flow valve incorporated therein near a proximal end thereof and an occlusive balloon near a distal end thereof, the manifold assembly comprising:
 (a) at least two hemostatic valves; and
 (b) a manifold body inclusive of a manifold, a first branch and a second branch such that (I) the manifold defines a main passageway wherein one of the hemostatic valves is sealingly disposed at each end thereof, the main passageway for permitting the proximal end of the intravascular device to be removably inserted therein through the hemostatic valve at one end with the proximal end protruding from the hemostatic valve at the other end such that the flow valve is located within the main passageway between the hemostatic valves; (II) the first branch defines an inflation/evacuation passageway in communication with the main passageway, the first branch being adapted for cooperation with (A) an evacuation syringe for selectively withdrawing a biocompatible gas from the intravascular device so as to selectively evacuate the occlusive balloon a plurality of times via the flow valve when in an open position and (B) an inflation syringe for selectively introducing a biocompatible gas under pressure into the intravascular device so as to selectively inflate the occlusive balloon a plurality of times via the flow valve when in the open position, the pressure within the occlusive balloon being maintainable when the flow valve is in the closed position; and (III) the second branch defines a pressure monitor passageway in communication with the main passageway, the pressure monitor passageway being adapted to enable a pressure gauge to be removably connectible thereto for monitoring pressure within the manifold assembly and, when the flow valve is situated in the main passageway and placed in the open position therein, within the intravascular device and the occlusive balloon near the distal end thereof.

24. The manifold assembly of claim 23 further including an intermediate positionable valve threadingly engaged to an end of the first branch through which the evacuation syringe and the inflation syringe are selectively enabled to communicate with the inflation/evacuation passageway of the manifold assembly.

* * * * *